United States Patent
Nishida et al.

(10) Patent No.: US 9,737,218 B2
(45) Date of Patent: Aug. 22, 2017

(54) BLOOD PRESSURE MEASUREMENT DEVICE, ELECTRONIC DEVICE, AND BLOOD PRESSURE MEASUREMENT METHOD

(71) Applicant: SEIKO EPSON CORPORATION, Tokyo (JP)

(72) Inventors: Kazuhiro Nishida, Matsumoto (JP); Sumio Utsunomiya, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/959,301

(22) Filed: Dec. 4, 2015

(65) Prior Publication Data

US 2016/0174854 A1   Jun. 23, 2016

(30) Foreign Application Priority Data

Dec. 17, 2014 (JP) ................. 2014-254708

(51) Int. Cl.
| | | |
|---|---|---|
| *A61B 5/021* | (2006.01) | |
| *A61B 5/026* | (2006.01) | |
| *A61B 5/00* | (2006.01) | |
| *A61B 5/02* | (2006.01) | |

(52) U.S. Cl.
CPC ...... *A61B 5/02108* (2013.01); *A61B 5/02007* (2013.01); *A61B 5/0261* (2013.01); *A61B 5/7242* (2013.01); *A61B 5/681* (2013.01)

(58) Field of Classification Search
None
See application file for complete search history.

(56) References Cited

U.S. PATENT DOCUMENTS

| | | | | |
|---|---|---|---|---|
| 6,953,435 | B2* | 10/2005 | Kondo | A61B 5/021 600/301 |
| 7,413,545 | B2* | 8/2008 | Muramatsu | A61B 5/02241 600/301 |
| 8,591,426 | B2* | 11/2013 | Onoe | A61B 5/02028 600/323 |
| 2010/0081940 | A1 | 4/2010 | McKenna | |
| 2010/0234744 | A1* | 9/2010 | Kawada | A61B 3/1241 600/500 |
| 2013/0211268 | A1 | 8/2013 | Fujii et al. | |

FOREIGN PATENT DOCUMENTS

| | | |
|---|---|---|
| JP | 2004-154231 A | 6/2004 |
| JP | 2004-201868 A | 7/2004 |
| JP | 2006-212095 A | 8/2006 |
| JP | 3910521 B2 | 4/2007 |

OTHER PUBLICATIONS

Apr. 15, 2016 Extended Search Report issued in European Patent Application No. 15200085.7.
Ola Larsson, "Digital Implementation of a Laser Doppler Perfusion Monitor," 2006.

* cited by examiner

*Primary Examiner* — Brian T Gedeon
(74) *Attorney, Agent, or Firm* — Oliff PLC

(57) ABSTRACT

A blood pressure measurement device includes: a light emitting unit configured to irradiate a living body with measurement light; a light receiving unit configured to receive reflected or transmitted light of the measurement light; and a computational unit configured to calculate a blood flow and a volume pulse wave based on a light-receiving result from the light receiving unit, and to calculate blood pressure based on the blood flow and blood vessel resistance that is obtained from the volume pulse wave.

15 Claims, 6 Drawing Sheets

BLOOD PRESSURE MEASUREMENT DEVICE, ELECTRONIC DEVICE, AND BLOOD PRESSURE MEASUREMENT METHOD

CROSS-REFERENCE

This application claims the benefit of Japanese Patent Application No. 2014-254708, filed on Dec. 17, 2014. The content of the aforementioned application is incorporated herein by reference in its entirety.

BACKGROUND

1. Technical Field

The present invention relates to a blood pressure measurement device and the like that measures blood pressure using light.

2. Related Art

Currently, a blood pressure measurement device, which is not a popular pressurizing type of blood pressure measurement device using a cuff but a new type of blood pressure measurement device using ultrasonic waves or light, has been in development (for example, refer to JP-A-2004-201868 and JP-A-2004-154231).

Devices disclosed in JP-A-2004-201868 and JP-A-2004-154231 adopt a technical method by which blood pressure is accurately measured without using a cuff, and require two sensors such as an ultrasonic wave sensor for measuring a blood flow velocity and an optical sensor for measuring a volume pulse wave. A blood pressure measurement device is highly demanded not only by medical institutions but also for home use, and a portable blood pressure measurement device is demanded. In order to cope with such a demand, it is desirable for a device to have as small a size as possible.

SUMMARY

An advantage of some aspects of the invention is to reduce the size of a blood pressure measurement device.

A first aspect of the invention is directed to a blood pressure measurement device including: a light emitting unit configured to irradiate a living body with light; a light receiving unit configured to receive light reflected in or transmitted through the living body; and a computational unit configured to calculate a blood flow and a volume pulse wave based on a light-receiving result from the light receiving unit, and to calculate blood pressure based on the blood flow and blood vessel resistance obtained from the volume pulse wave.

As another aspect of the invention, the aspect of the invention maybe configured as a blood pressure measurement method that is executed by a device including a light emitting unit configured to irradiate a living body with light and a light receiving unit configured to receive light reflected in or transmitted through the living body, the method including: calculating a blood flow and a volume pulse wave based on a light-receiving result from the light receiving unit; and calculating blood pressure based on the blood flow and blood vessel resistance that is obtained from the volume pulse wave.

According to the first aspect of the invention and the like, it is possible to calculate the blood flow and the volume pulse wave based on the light-receiving result from the light receiving unit, and to calculate the blood pressure based on the blood flow and the volume pulse wave. That is, it is possible to measure the blood pressure using one light receiving unit. Accordingly, it is possible to further reduce the size of the device compared to a device of the related art which requires two sensors such as an ultrasonic wave sensor for measuring a blood flow velocity and an optical sensor for measuring a volume pulse wave as disclosed in the aforementioned Patent Documents of the related art.

A second aspect of the invention is directed to the blood pressure measurement device according to the first aspect of the invention, in which the computational unit analyzes the frequency of light received by the light receiving unit, and calculates the blood flow using a frequency analysis result.

Specifically, as a third aspect of the invention, the blood pressure measurement device according to the second aspect of the invention may be configured such that the computational unit calculates the blood flow using Expression $$Q = K_Q \frac{\int_{f_1}^{f_2} f \cdot P(f) df}{\langle I^2 \rangle} \quad (1)$$

Here, Q represents a blood flow, $K_Q$ represents a constant, $f_1$ and $f_2$ represent cutoff frequencies, $\langle I^2 \rangle$ represents the mean square of the intensity of received light, and P(f) represents a power spectrum.

According to the second aspect or the third aspect of the invention, it is possible to calculate the blood flow using a so-called laser Doppler technique.

A fourth aspect of the invention is directed to the blood pressure measurement device according to any one of the first to third aspects of the invention, in which the computational unit calculates the blood vessel resistance based on two amplitudes of the volume pulse wave, with the two amplitudes corresponding to a forward wave and a reflected wave, respectively.

Specifically, as a fifth aspect of the invention, the blood pressure measurement device according to the fourth aspect of the invention may be configured such that the computational unit calculates the blood vessel resistance based on a ratio between the two amplitudes.

According to the fourth aspect or the fifth aspect of the invention, it is possible to calculate the blood vessel resistance using the ratio between the amplitude of a spot (time) indicating the forward wave and the amplitude of a spot (time) indicating the reflected wave in the volume pulse wave. The reason for this is that the amplitude ratio is a value which correlates to the blood vessel resistance.

A sixth aspect of the invention is directed to an electronic device including: a main unit; and a band portion configured to mount the main unit on a measurement site of a living body. The main unit includes a light emitting unit configured to irradiate the living body with light; a light receiving unit configured to receive light reflected in or transmitted through the living body, and a computational unit configured to calculate a blood flow and a volume pulse wave based on a light-receiving result from the light receiving unit, and to calculate blood pressure based on the blood flow and blood vessel resistance that is obtained from the volume pulse wave.

According to the sixth aspect of the invention, it is possible to realize the electronic device that provides the same effects as in the first aspect of the invention. The main unit can be mounted on the measurement site of the living body using the band portion, and thus, for example, the entire shape of the electronic device can be the shape of a wrist watch, and the electronic device can be configured to have good portability. With this configuration, a location or an amount of time does not matter, and thus it is possible to measure blood pressure continuously or on a regular basis (periodically) for a relatively long period of time.

A seventh aspect of the invention is directed to an electronic device in which an optical probe and a main device are communicatively connected to each other. The optical probe includes a light emitting unit configured to irradiate a living body with light, and a light receiving unit configured to receive light reflected in or transmitted through the living body. The main device includes a computational unit configured to calculate a blood flow and a volume pulse wave based on a light-receiving result from the light receiving unit, and to calculate blood pressure based on the blood flow and blood vessel resistance obtained from the volume pulse wave.

According to the seventh aspect of the invention, it is possible to realize the electronic device that provides the same effects as in the first aspect of the invention.

An eighth aspect of the invention is directed to an electronic device including the blood pressure measurement device according to any one of the first to fifth aspects.

According to the eighth aspect of the invention, it is possible to realize the electronic device that provides the same effects as in the first to fifth aspects of the invention.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
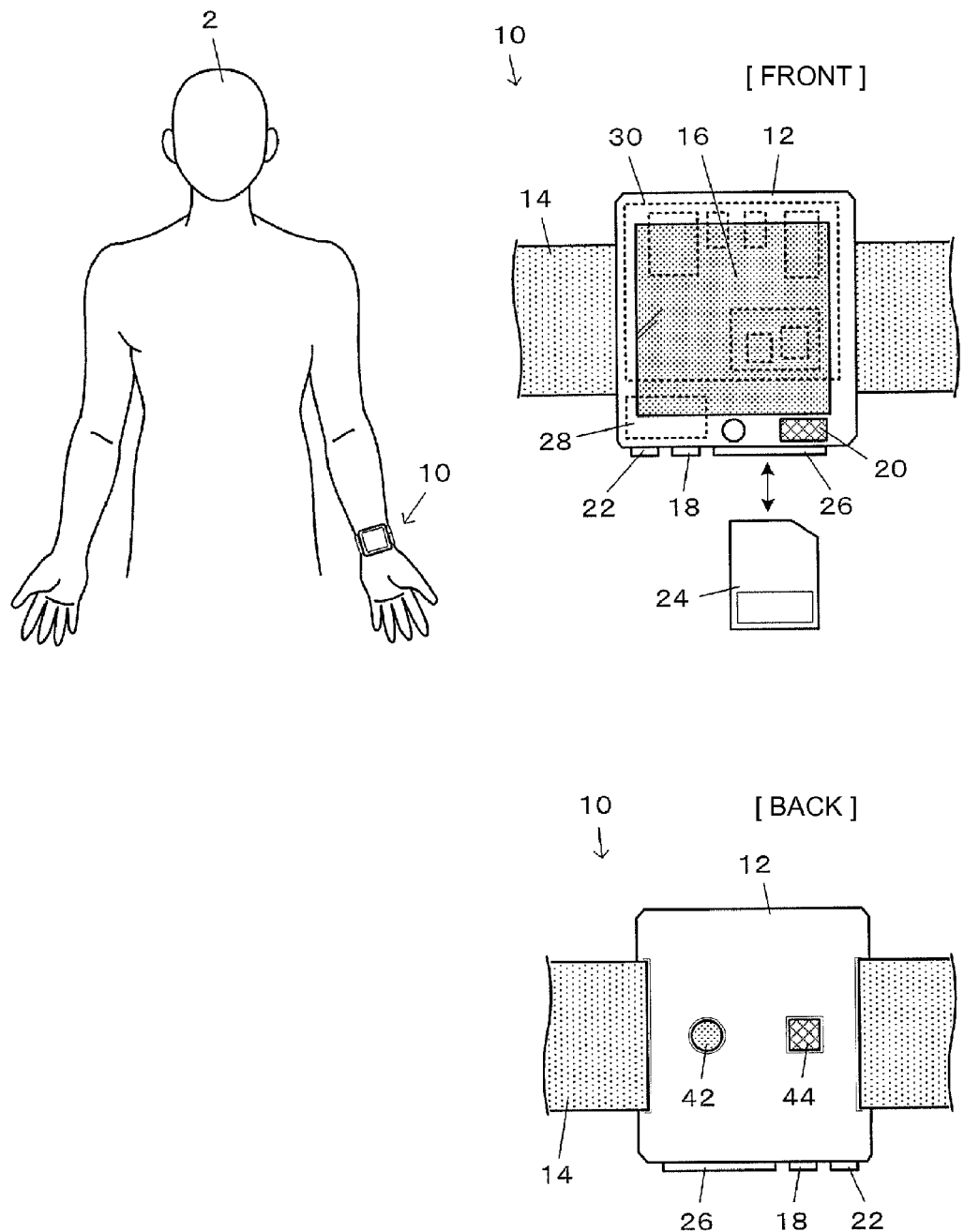
FIG. 1 is a view illustrating the entire configuration of a blood pressure measurement device.

FIG. 1 is an exterior view illustrating an example of the entire configuration of a blood pressure measurement device 10 in an embodiment. The blood pressure measurement device 10 is an electronic device that non-invasively measures the blood pressure of a subject 2 using light. As illustrated in FIG. 1, the blood pressure measurement device 10 is a wrist-watch type of blood pressure measurement device, and is configured to include a body case 12, and a fixing band 14 that is a band portion having a hook-and-loop fastener to mount and fix the body case 12 to a measurement site such as the wrist, the arm, or the like of the subject 2.

A touch panel 16, an operation switch 18, or a speaker 20 are provided on a front surface (a surface facing the outside when the subject 2 wears the blood pressure measurement device 10) of the body case 12. The subject 2 inputs an instruction indicating the start of a measurement using the touch panel 16 or the operation switch 18, voice guidance for measurement is output through the speaker 20, or a measurement result is displayed on the touch panel 16.

A side surface of the body case 12 is provided with a communication device 22 for communicating with external devices, and a reader/writer 26 for a memory card 24. The communication device 22 is realized by a jack to which a cable for wired communication is connected, or a wireless communication module for wireless communication and an antenna thereof. The memory card 24 is a data re-writable non-volatile memory such as a flash memory, a ferroelectric random access memory (FeRAM), or a magnetoresistive random access memory (MRAM).

A light emitting unit 42 and a light receiving unit 44 are provided on a back surface of the body case 12 in such a way that the light emitting unit 42 and the light receiving unit 44 can come into contact with the skin surface of the subject 2. The light emitting unit 42 irradiates the subject 2, which is a living body, with measurement light. For example, the light emitting unit 42 is realized by a laser beam source that irradiates (emits) a laser beam with a predetermined short wavelength. In the embodiment, a living body is preferably irradiated with a laser beam having a near-infrared bandwidth which has skin transmittance. The light receiving unit 44 receives transmitted light, representing measurement light which transmits through the tissues in a living body, or light reflected by the tissues in the living body, and outputs an electric signal according to the amount of received light. The light receiving unit 44 is realized by an imaging element such as a charge coupled device (CCD) or a complementary metal oxide semiconductor (CMOS).

Figure 2:
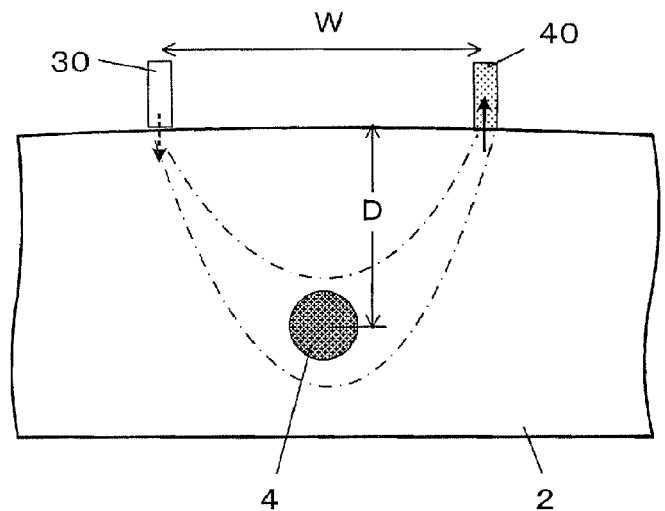
FIG. 2 is a view illustrating a light transmission path between a light emitting unit and a light receiving unit.

The light emitting unit 42 and the light receiving unit 44 are provided corresponding to the assumed position of a blood vessel (for example, the radial artery in the wrist of the subject 2) which is a measurement target. Specifically, FIG. 2 is a view illustrating the transmission of light through a living body, and illustrates a section taken along a depth direction of the living body of the subject 2. Measurement light irradiated by the light emitting unit 42 enters the living body through the skin surface, diffuses therein, and is reflected in the living body. Only a fraction of the measurement light reaches the light receiving unit 44. A transmission path of the light forms the shape (a region interposed between two arcs) of a banana, and the vicinity of substantially the center of the transmission path has the maximum width in the depth direction. A depth (light-reachable depth) D of this transmission path is decreased to the extent that a gap W between a light emitting element and a light receiving element is small. The depth D is increased to the extent that the gap W is large. A blood vessel 4 desirably passes through the vicinity of the center of the transmission path of light from the light emitting unit 42 to the light receiving unit 44, with the vicinity of the center having the maximum width in the depth direction. Accordingly, the blood vessel, a measurement target, is positioned substantially at the center of the gap between the light emitting unit 42 and the light receiving unit 44, and the positions of the light emitting unit 42 and the light receiving unit 44 are determined in such a way that the gap W becomes a distance corresponding to the depth D of the blood vessel. For example, when it is assumed that the depth D of the blood vessel 4 is approximately 3 [mm], the gap W can be approximately 5 [mm] to approximately 6 [mm].

A rechargeable battery 28 and a control substrate 30 are built into the body case 12. With regard to a charging method of the battery 28, the battery 28 maybe configured such that an electric contact is provided on the back surface of the body case 12, the blood pressure measurement device 10 is set in a cradle connected to a domestic power supply, and the battery 28 is charged with electricity via the cradle and the electric contact. Alternatively, the battery 28 may be wirelessly charged with electricity.

A central processing unit (CPU), a main memory, a measurement data memory, a touch panel controller, and a sensor module controller are mounted on the control substrate 30. The main memory is a storage medium capable of storing a program, initial data, or computational values of the CPU, and is realized by a random access memory (RAM), a read only memory (ROM), a flash memory, or the like. The memory card 24 may be configured to store the program or the initial data. The measurement data memory is a storage medium for storing measurement data, and is realized by a data re-writable non-volatile memory such as a flash memory, an FeRAM, or an MRAM. The memory card 24 may be configured to store the measurement data.

Principle (A) Calculation of Blood Pressure

As illustrated by Expression (2) hereinbelow, blood pressure Pr is represented by the product of a blood flow Q and peripheral blood vessel resistance R.

$$P_R = Q \times R \tag{2}$$

Blood Flow Q

The blood flow Q is calculated using a laser Doppler method. Specifically, a power spectrum (frequency spectrum) P(f) is calculated by performing a frequency analysis process such as fast Fourier transform (FFT) on a light-receiving signal (signal representing a change in the amount of received light over time) from the light receiving unit 44. The blood flow Q is obtained using Expression (3) hereinbelow based on the calculated power spectrum P(f).

$$Q = K_Q \frac{\int_{f_1}^{f_2} f \cdot P(f) df}{\langle I^2 \rangle} \tag{3}$$

In Expression (3), "$K_Q$" represents a predetermined constant, "$f_1$ and $f_2$" represent the cutoff frequencies of a bandpass filter, and "$\langle I^2 \rangle$" represents the mean square of the intensity of received light.

(C) Peripheral Blood Vessel Resistance R

The peripheral blood vessel resistance R is calculated using a volume pulse wave. Specifically, the blood vessel repeatedly constricts and expands due to a heartbeat, and the blood flow in the blood vessel changes in response thereto. That is, when a site in the blood vessel is continuously irradiated with measurement light, the amount of light passing through the blood vessel changes due to a change in the blood flow. The blood vessel is irradiated with measurement light from the light emitting unit 42, and a volume pulse wave is detected based on a change in the amount of light received by the light receiving unit 44 at that time. The volume pulse wave may be calculated by performing a frequency filtering process or a smoothing process on a light-receiving signal from the light receiving unit 44.

Figure 3:
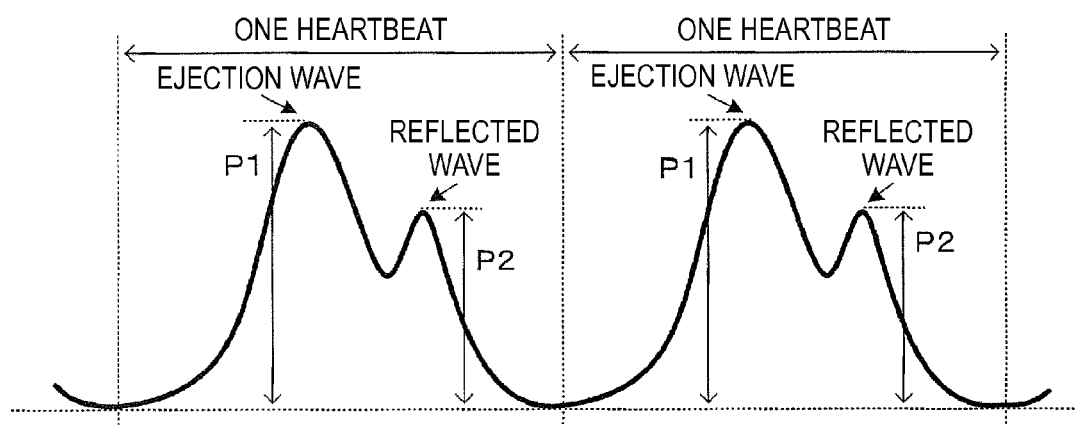
FIG. 3 is an example of a volume pulse wave.

FIG. 3 is an example of the volume pulse wave. As illustrated in FIG. 3, the volume pulse wave is a periodic function having a heartbeat period of the heart as a period. Two peaks respectively caused by a forward wave and a reflected wave appear in a single period of a waveform. A systolic period refers to when the peak of the forward wave appears, and a diastolic period refers to when the peak of the reflected wave appears. It is understood that a ratio (=P2/P1) between an amplitude P1 of the forward wave and an amplitude P2 of the reflected wave correlates to the peripheral blood vessel resistance R. The reason for this is that the level of the reflected wave changes according to the peripheral blood vessel resistance R. For this reason, in the embodiment, the peripheral blood vessel resistance R is calculated using this amplitude ratio. Specifically, as illustrated in Expression (4) hereinbelow, the peripheral blood vessel resistance R is calculated based on a function f(x) having the amplitude ratio as a variable x.

$$R = f\left(\frac{P_2}{P_1}\right) \tag{4}$$

In the embodiment, Expression (4) is simplified into Expression (5) hereinbelow, and the peripheral blood vessel resistance R is approximately proportional to the amplitude ratio.

$$R \approx K\left(\frac{P_2}{P_1}\right) \tag{5}$$

In Expression (5), constant K may have a fixed value, or may be determined by calibrating the blood pressure measurement device 10 using a pressurizing type of blood pressure monitor prior to measuring blood pressure.

Functional Configuration

Figure 4:
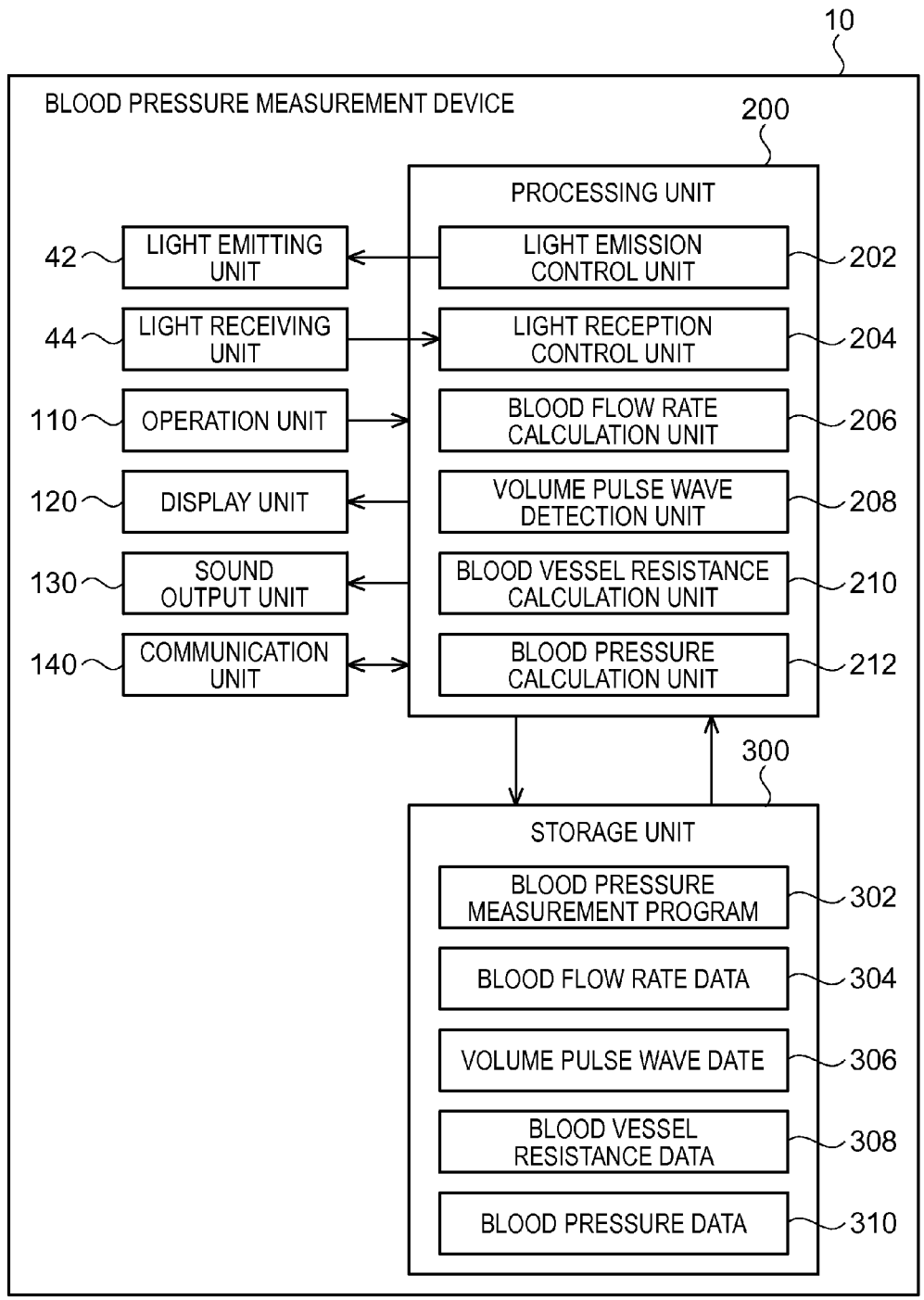
FIG. 4 is a diagram illustrating the functional configuration of the blood pressure measurement device.

FIG. 4 is a diagram illustrating the functional configuration of the blood pressure measurement device 10. In FIG. 4, the blood pressure measurement device 10 is configured to include an operation unit 110; a display unit 120; a sound output unit 130; a communication unit 140; the light emitting unit 42; the light receiving unit 44; a processing unit 200; and a storage unit 300.

The operation unit 110 is a button switch, a touch panel, or an input device for various sensors, and outputs an operation signal to the processing unit 200 according to a performed operation. Various instructions such as an instruction indicating the start of a blood pressure measurement are input through the operation unit 110. In FIG. 1, the operation switch 18 and the touch panel 16 are equivalent to the operation unit 110.

The display unit 120 is a display device such as a liquid crystal display (LCD), and displays various pieces of information based on a display signal from the processing unit 200. The display unit 120 displays a measurement result. In FIG. 1, the touch panel 16 is equivalent to the display unit 120.

The sound output unit 130 is a sound output device such as a speaker, and outputs various sounds based on a sound signal from the processing unit 200. The sound output unit 130 outputs a notification sound or a guide voice such as the start or the end of measurement of biological information.

The communication unit 140 is a communication device such as a wireless communicator, a modem, a jack of a communication cable for wired communication, and a control circuit, and communicates with external devices while being connected to a communication line. In FIG. 1, the communication device 22 is equivalent to the communication unit 140.

The processing unit 200 is realized by electronic components such as mircoprocessors, for example, a CPU and a graphics processing unit (GPU), an application specific integrated circuit (ASIC), a field-programmable gate array (FPGA), and an IC memory. The processing unit 200 controls the operation of the blood pressure measurement device 10 by executing various computational processes based on a predetermined program, data, an operation signal from the operation unit 110, and the like. In FIG. 1, the control substrate 30 is equivalent to the processing unit 200. The processing unit 200 includes a light emission control unit 202; a light reception control unit 204; a blood flow calculation unit 206; a volume pulse wave detection unit 208; a blood vessel resistance calculation unit 210; and a blood pressure calculation unit 212.

The light emission control unit 202 controls the light emitting unit 42 such that the irradiation of measurement light is started and ended, the intensity of the measurement light is adjusted, and the like. The light reception control unit 204 controls the light reception of the light receiving unit 44. When receiving a signal according to the amount of received light from the light receiving unit 44, the light emitting unit 42 performs a filtering process such as the removal of noise, a conversion process for the conversion of signals to digital signals, and the like. In the description hereinbelow, a light-receiving result (light-receiving signal) of the light receiving unit 44 may be a signal input from the light receiving unit 44, or may be a signal that undergoes a signal process performed by the light reception control unit 204. The reason for this is that these signals are deemed to be substantially equivalent.

The blood flow calculation unit 206 calculates the blood flow Q based on the light-receiving result from the light receiving unit 44. That is, the blood flow calculation unit 206 calculates the power spectrum (frequency spectrum) P(f) by performing a frequency analysis process called FFT on the light-receiving signal from the light receiving unit 44. The blood flow Q is calculated according to Expression (3) using the power spectrum P(f). The calculated blood flow Q is stored as blood flow data 304.

The volume pulse wave detection unit 208 detects a volume pulse wave based on the light-receiving result from the light receiving unit 44. Specifically, the volume pulse wave detection unit 208 causes the light emission control unit 202 to drive a measurement light emitting element 52a such that light is emitted, and detects a change in the amount of received light (the intensity of a light-receiving signal) of the measurement light receiving element 58a at that time as a volume pulse wave. The detected volume pulse wave is stored as volume pulse wave data 306.

The blood vessel resistance calculation unit 210 calculates the peripheral blood vessel resistance R based on the volume pulse wave detected by the volume pulse wave detection unit 208. Specifically, the blood vessel resistance calculation unit 210 calculates an amplitude ratio between an amplitude P1 and an amplitude P2 from one heartbeat waveform of the volume pulse wave. Herein, the amplitude P1 represents the amplitude of a peak corresponding to a forward wave, and the amplitude P2 represents the amplitude of a peak corresponding to a reflected wave. The blood vessel resistance calculation unit 210 calculates the peripheral blood vessel resistance R according to Expression (5) using this amplitude ratio. The calculated peripheral blood vessel resistance R is stored as blood vessel resistance data 308. An average value of the amplitudes P1 and the amplitudes P2 of a plurality of heartbeat waveforms may be adopted instead of a value obtained from one heartbeat waveform.

The blood pressure calculation unit 212 calculates blood pressure Pr according to Expression (2) using the blood flow Q calculated by the blood flow calculation unit 206 and the peripheral blood vessel resistance R calculated by the blood vessel resistance calculation unit 210. The calculated blood pressure Pr is accumulated and stored as blood pressure data 310 associated with a measurement time.

The storage unit 300 is a storage device such as a ROM, a RAM, or a hard disk. The storage unit 300 stores a program executed by the processing unit 200 to integrally control the blood pressure measurement device 10, data, and the like, is used as a working region of the processing unit 200, and temporarily stores the results of computations executed by the processing unit 200, operation data from the operation unit 110, and the like. In FIG. 1, the main memory and the measurement data memory mounted on the control substrate 30 are equivalent to the storage unit 300. The storage unit 300 stores the blood pressure measurement program 302, the blood flow data 304, the volume pulse wave data 306, the blood vessel resistance data 308, and the blood pressure data 310.

Flow of Process

Figure 5:
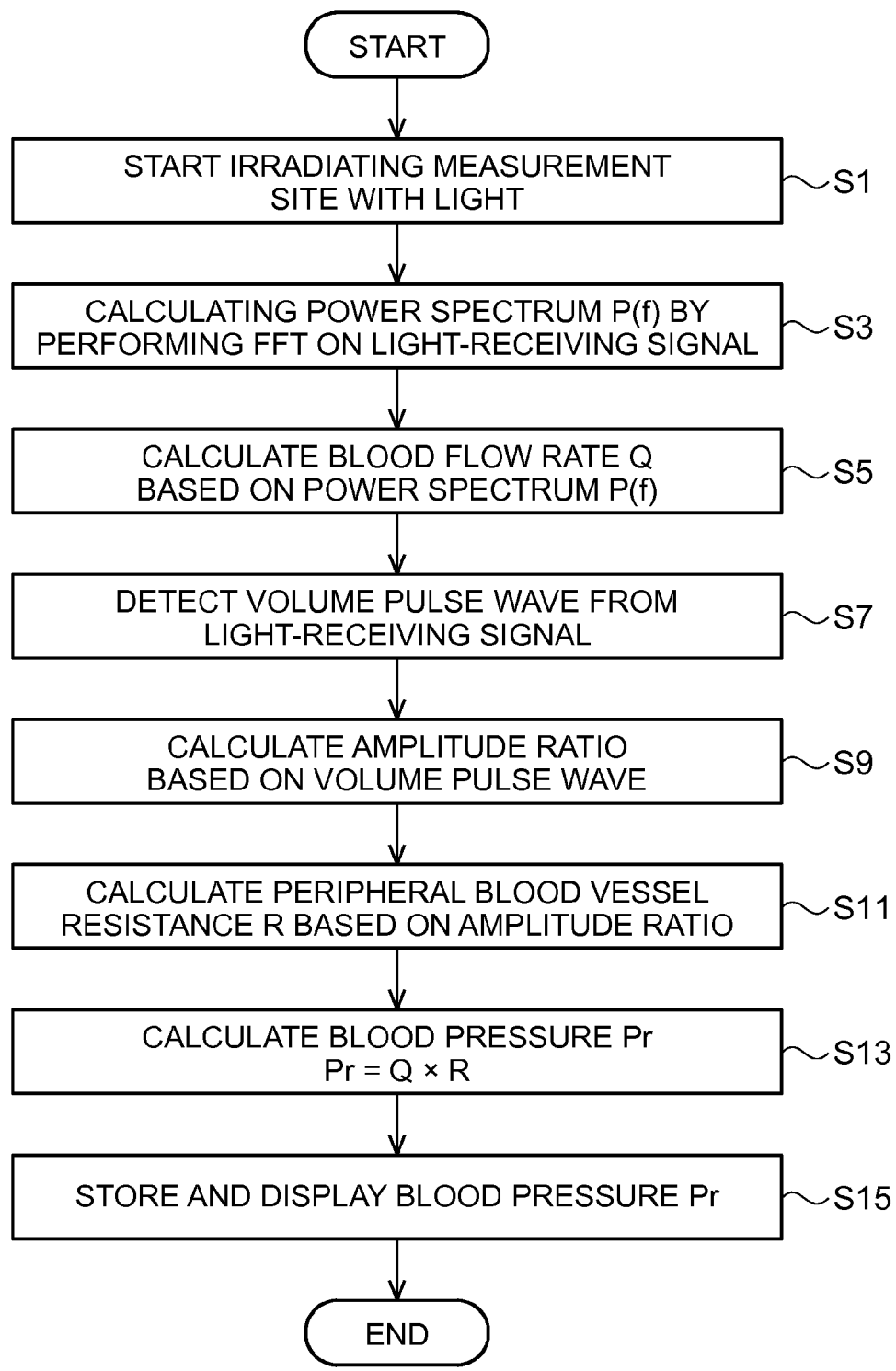
FIG. 5 is a flowchart of a blood pressure measurement process.

FIG. 5 is a flowchart illustrating the flow of a blood pressure measurement process. The processing unit 200 executes steps according to the blood pressure measurement program 302 such that this process is realized. The blood pressure measurement device 10 is mounted and fixed to a measurement site by the fixing band 14 in such a way that the light emitting unit 42 and the light receiving unit 44 come in close contact with the measurement site which is the wrist of the subject 2. In this state, when a predetermined instruction indicating the start of a measurement is initiated, the blood pressure measurement process starts.

First, the processing unit 200 causes the light emitting unit 42 to start irradiating the measurement site with measurement light, and acquires a light-receiving result (light-receiving signal) from the light receiving unit 44 at that time (step S1). The blood flow calculation unit 206 calculates the power spectrum P(f) by performing the frequency analysis process such as FFT on the light-receiving signal from the light receiving unit 44 (step S3). Subsequently, the blood flow Q is calculated according to Expression (3) using the power spectrum P(f) (step S5).

The volume pulse wave detection unit 208 detects a volume pulse wave based on the light-receiving signal from the light receiving unit 44 (step S7). Subsequently, the blood vessel resistance calculation unit 210 calculates an amplitude ratio between the amplitude of a forward wave and the amplitude of a reflected wave from the detected volume pulse wave (step S9), and calculates the peripheral blood vessel resistance R according to Expression (5) using this amplitude ratio (step S11).

Thereafter, the blood pressure calculation unit 212 calculates the blood pressure Pr according to Expression (2) using the calculated blood flow Q and the calculated peripheral blood vessel resistance R (step S13). The calculated blood pressure Pr is displayed on the display unit 120, and is stored in the storage unit 300 (step S15). When the aforementioned steps have been performed, this process ends.

The blood pressure measurement process illustrated in FIG. 5 is a process of performing a blood pressure measurement once for one instruction indicating the start of a measurement; however, a blood pressure measurement may be continuously executed until an instruction indicating the end of the measurement is initiated after an instruction indicating the start of the measurement is initiated. That is, when an instruction indicating the end of the measurement is not initiated after step S15, the process may proceed to step S1.

Operational Effects

As such, according to the blood pressure measurement device 10 of the embodiment, the light emitting unit 42 irradiates a measurement site with measurement light, and the blood flow Q and the volume pulse wave are calculated based on a light-receiving result from the light receiving unit 44, and thus the blood pressure Pr can be calculated based on the calculation results. That is, it is possible to measure the blood pressure using a detection result from one optical sensor. Accordingly, it is possible to reduce the size of the device compared to a device of the related art which requires two sensors such as an ultrasonic wave sensor for measuring a blood flow velocity and an optical sensor for measuring a volume pulse wave as disclosed in the aforementioned Patent Documents.

Modification Example

The application of the invention is not limited to the aforementioned embodiment, and naturally, various forms of modifications can be made to the invention insofar as the modifications do not depart from the purport of the invention.

(A) Measurement of Oxygen Saturation

Figure 6:
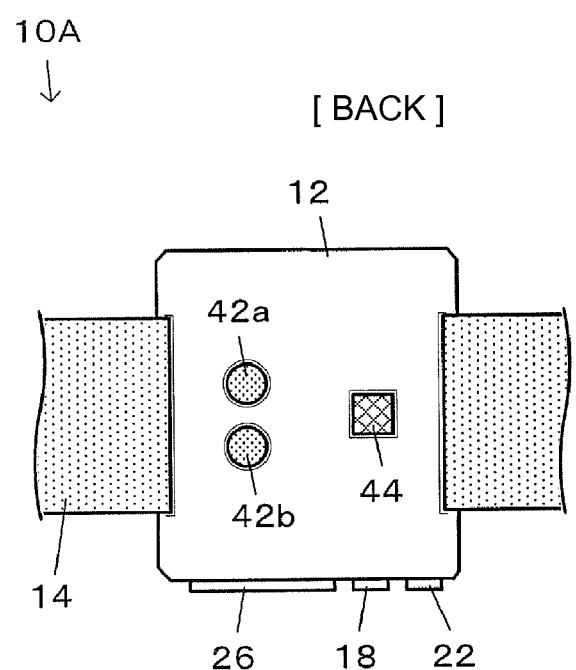
FIG. 6 is another example of the configuration of a blood pressure measurement device.

In addition, oxygen saturation maybe measured. FIG. 6 is an example of the configuration of a blood pressure measurement device 10A that is also capable of measuring oxygen saturation, and illustrates the back surface of the body case 12. As illustrated in FIG. 6, two light emitting units 42a and 42b are provided on the back surface of the body case 12 of the blood pressure measurement device 10A. The two light emitting units 42a and 42b irradiate a measurement site with beams of measurement light (laser beams) with different wavelengths $\lambda 1$ and $\lambda 2$, respectively. Specifically, the measurement site is irradiated with red light (R) with the wavelength $\lambda 1$ and near infrared light (IR) with the wavelength $\lambda 2$. The light emitting units 42a and 42b are controlled such that the measurement site is alternately irradiated with beams of measurement light, and the light receiving unit 44 receives reflected or transmitted light corresponding to either of the beams of measurement light from the light emitting units 42a and 42b.

A volume pulse wave F1 and a blood flow Q1, which correspond to the measurement light with the wavelength $\lambda 1$ irradiated by the light emitting unit 42a, and a volume pulse wave F1 and a blood flow Q2, which correspond to the measurement light with the wavelength $\lambda 2$ irradiated by the light emitting unit 42b, are obtained. Oxygen saturation (blood oxygen concentration) SpO2 can be calculated based on the difference between the absorbance of the measurement light with the wavelength $\lambda 1$ and the absorbance of the measurement light with the wavelength $\lambda 2$ under the principle of a well-known pulse oximeter using the volume pulse wave F1/the blood flow Q1 and the volume pulse wave F2/the blood flow Q2 which respectively correspond to two wavelengths $\lambda 1$ and $\lambda 2$. As described in the embodiment, the blood pressure Pr can be obtained based on the volume pulse wave F and the blood flow Q corresponding to either of the beams of measurement light with the wavelengths $\lambda 1$ and $\lambda 2$.

(B) Entire Configuration of Blood Pressure Measurement Device

In the aforementioned embodiment, the blood pressure measurement device 10 is a wrist-watch type of electronic device; however, the blood pressure measurement device 10 may be a different type of blood pressure measurement device. For example, the blood pressure measurement device 10 may be an electronic device which is configured such that a probe and a main device are separately built, and are communicatively connected to each other.

Figure 7:
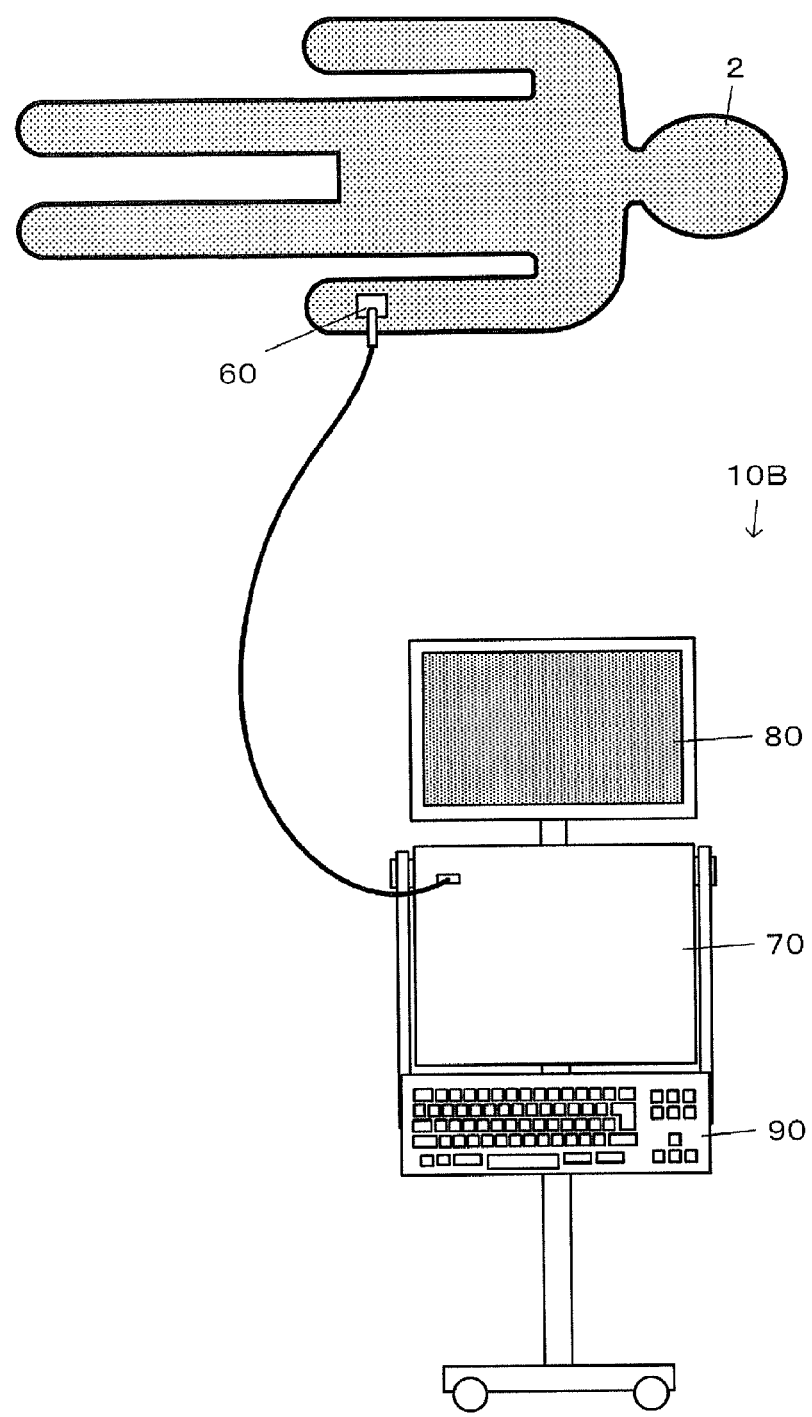
FIG. 7 is still another example of the configuration of a blood pressure measurement device.

FIG. 7 is another example of the configuration of the blood pressure measurement device 10. In FIG. 7, a blood pressure measurement device 10B is an electronic device that includes an optical probe 60; amain device 70; a video monitor 80; and a keyboard 90. The main device 70 may be configured to include the video monitor 80 and the keyboard 90.

The optical probe 60 is a thin flat pad type of optical probe that can be attached to the wrist or the like, which is a measurement site of the subject 2, and the optical probe 60 is used while being attached and fixed to the measurement site of the subject 2. The light emitting unit 42 and the light receiving unit 44 are built into the optical probe 60. Similarly to the blood pressure measurement device 10 in the aforementioned embodiment, the light emitting unit 42 and the light receiving unit 44 are fixed to the subject 2 in such a way that the light emitting unit 42 and the light receiving unit 44 come into close contact with the skin surface of the subject 2. The optical probe 60 is configured such that the light emitting unit 42 irradiates a measurement site with measurement light according to a light emission control signal from the main device 70, and the light receiving unit 44 outputs a light-receiving signal (the amount of received light) to the main device 70. The optical probe 60 may not be an attachable pad type of optical probe, but may be a pen type of optical probe that is held by the hand of an operator and is brought into contact with a measurement site of the subject 2.

The main device 70 is realized by various microprocessors, ASIC's, and electronic circuits such as a CPU, a GPU, and a digital signal processor (DSP); information storage media such as various IC memories (for example, a VRAM, a RAM, and a ROM) and a hard disk; interface IC's and connection terminals for transmitting to and receiving data from external devices; a power supply circuit; and the like. The main device 70 has the functions of the processing unit 200, the storage unit 300, and the communication unit 140 illustrated in FIG. 4.

The main device 70 is connected to the optical probe 60 via a cable. The main device 70 performs optical measurement using the optical probe 60, detects a volume pulse wave, sets optimum pressing force, calculates biological information (blood glucose level), and displays a calculation result on the video monitor 80.

The video monitor 80 is an image display device, and is realized by a flat panel display or a touch panel display. A speaker may be appropriately built into the video monitor 80.

The keyboard 90 is a unit through which an operator inputs various operations.

In the example illustrated in FIG. 7, the keyboard 90 is swingably supported by a swing arm, as necessary, is lifted in front of an operator, and is used; however, the keyboard 90 may be integrated with the main device 70, or the video monitor 80 may be formed of a touch panel such that the video monitor 80 serves as the keyboard 90. In addition, other operation input devices such as a mouse and a track pad can be added.

The operation and the process content of the blood pressure measurement device 10B is the same as those of the blood pressure measurement device 10.

What is claimed is:
1. A blood pressure measurement device comprising:
 a light emitting unit configured to irradiate a living body with light;
 a light receiving unit configured to receive light reflected in or transmitted through the living body; and
 a computational unit configured to calculate a blood flow and a volume pulse wave based on a light-receiving result from the light receiving unit, and to calculate blood pressure based on the blood flow and a blood vessel resistance that is obtained from the volume pulse wave.

2. The blood pressure measurement device according to claim 1, wherein the computational unit analyzes the frequency of light received by the light receiving unit, and calculates the blood flow using a frequency analysis result.

3. The blood pressure measurement device according to claim 2, wherein the computational unit calculates the blood flow using Expression (1), $$Q = K_Q \frac{\int_{f_1}^{f_2} f \cdot P(f) df}{\langle I^2 \rangle} \quad (1)$$

here, Q represents a blood flow, $K_Q$ represents a constant, $f_1$ and $f_2$ represent cutoff frequencies, $\langle I^2 \rangle$ represents the mean square of the intensity of received light, and P(f) represents a power spectrum.

4. The blood pressure measurement device according to claim 1, wherein the computational unit calculates the blood vessel resistance based on two amplitudes of the volume pulse wave, with the two amplitudes corresponding to a forward wave and a reflected wave, respectively.

5. The blood pressure measurement device according to claim 4, wherein the computational unit calculates the blood vessel resistance based on a ratio between the two amplitudes.

6. An electronic device comprising:
a main unit; and
a band portion configured to mount the main unit on a measurement site of a living body,
wherein the main unit includes:
a light emitting unit configured to irradiate the living body with light,
a light receiving unit configured to receive light reflected in or transmitted through the living body, and
a computational unit configured to calculate a blood flow and a volume pulse wave based on a light-receiving result from the light receiving unit, and to calculate blood pressure based on the blood flow and a blood vessel resistance that is obtained from the volume pulse wave.

7. An electronic device in which an optical probe and a main device are communicatively connected to each other, wherein the optical probe includes:
a light emitting unit configured to irradiate a living body with light, and
a light receiving unit configured to receive light reflected in or transmitted through the living body, and
the main device includes a computational unit configured to calculate a blood flow and a volume pulse wave based on a light-receiving result from the light receiving unit, and to calculate blood pressure based on the blood flow and a blood vessel resistance obtained from the volume pulse wave.

8. An electronic device including the blood pressure measurement device according to claim 1.

9. An electronic device including the blood pressure measurement device according to claim 2.

10. An electronic device including the blood pressure measurement device according to claim 3.

11. An electronic device including the blood pressure measurement device according to claim 4.

12. An electronic device including the blood pressure measurement device according to claim 5.

13. A blood pressure measurement method that is executed by a device including a light emitting unit configured to irradiate a living body with light and a light receiving unit configured to receive light reflected in or transmitted through the living body, the method comprising:
calculating a blood flow and a volume pulse wave based on a light-receiving result from the light receiving unit; and
calculating blood pressure based on the blood flow and a blood vessel resistance that is obtained from the volume pulse wave.

14. A blood pressure measurement device comprising:
a light emitting unit configured to irradiate a living body with light;
a light receiving unit configured to receive light reflected in or transmitted through the living body; and
a computational unit configured to calculate a blood flow and a volume pulse wave based on a light-receiving result from the light receiving unit, and to calculate blood pressure based on the blood flow and a blood vessel resistance that is obtained from the volume pulse wave,
wherein the computational unit analyzes the frequency of light received by the light receiving unit, and calculates the blood flow using a frequency analysis result, and
the computational unit calculates the blood flow using Expression (1), $$Q = K_Q \frac{\int_{f_1}^{f_2} f \cdot P(f) df}{\langle I^2 \rangle} \quad (1)$$

here, Q represents a blood flow, $K_Q$ represents a constant, $f_1$ and $f_2$ represent cutoff frequencies, $\langle I^2 \rangle$ represents the mean square of the intensity of received light, and P(f) represents a power spectrum.

15. A blood pressure measurement device comprising:
a light emitting unit configured to irradiate a living body with light;
a light receiving unit configured to receive light reflected in or transmitted through the living body; and
a computational unit configured to calculate a blood flow and a volume pulse wave based on a single light-receiving result from the light receiving unit, and to calculate blood pressure based on the blood flow and a blood vessel resistance that is obtained from the volume pulse wave of the single light-receiving result.

* * * * *